US00PP37824P2

(12) United States Plant Patent
von Tubeuf

(10) Patent No.: US PP37,824 P2
(45) Date of Patent: Oct. 27, 2026

(54) POINSETTIA PLANT NAMED 'NPCW25442'

(50) Latin Name: *Euphorbia pulcherrima*
Varietal Denomination: NPCW25442

(71) Applicant: KLEMM + SOHN GMBH & CO. KG, Stuttgart (DE)

(72) Inventor: Guido von Tubeuf, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/460,971

(22) Filed: Jan. 27, 2026

(51) Int. Cl.
*A01H 5/02* (2018.01)
*A01H 6/38* (2018.01)

(52) U.S. Cl.
USPC ..... Plt./307
CPC ..... *A01H 6/385* (2018.05)

(58) Field of Classification Search
USPC ..... Plt./307
CPC ..... A01H 5/0244
See application file for complete search history.

*Primary Examiner* — Kent L Bell
(74) *Attorney, Agent, or Firm* — Weatherly IP Solutions, LLC; Karen P. Bechtold; James M. Weatherly

(57) ABSTRACT

A new poinsettia plant particularly distinguished by dark red bracts and a wide, moderately upright habit, is disclosed.

1 Drawing Sheet

Genus and species: *Euphorbia pulcherrima.*
Variety denomination: 'NPCW25442'.

BACKGROUND OF THE NEW PLANT

The present invention comprises a new and distinct variety of poinsettia, botanically known as *Euphorbia pulcherrima* and hereinafter referred to by the variety name 'NPCW25442'. 'NPCW25442' was identified in Nairobi, Kenya in December 2020 as a cross-pollination from female parent 'EP-2016-6142' (unpatented) and male parent 'NPCW19282' (U.S. Plant Pat. No. 32,726). A seedling was selected in October 2021 and named 'NPCW25442'.

In May 2022, 'NPCW25442' was first vegetatively propagated by apical cuttings in Stuttgart, Germany and was found to reproduce true to type in successive generations of asexual propagation.

SUMMARY

The following are the most outstanding and distinguishing characteristics of this new variety when grown under normal horticultural practices in Stuttgart, Germany.

1. Dark red colored bracts, and
2. Wide, moderately upright habit.

DESCRIPTION OF THE PHOTOGRAPH

This new poinsettia plant is illustrated by the accompanying photograph which shows an overall view of the plant. The photograph is of a plant approximately seventeen-weeks-old, grown indoors in Stuttgart, Germany in November 2025. The colors shown are as true as can be reasonably obtained by conventional photographic procedures.

DESCRIPTION OF THE NEW VARIETY

The following detailed descriptions set forth the distinctive characteristics of 'NPCW25442'. The data which define these characteristics were collected from asexual reproductions carried out in Stuttgart, Germany. Data was collected on seventeen- to nineteen-week-old plants grown indoors in Stuttgart, Germany under greenhouse conditions in November 2025. Color references are to The R.H.S. Colour Chart of The Royal Horticultural Society of London (R.H.S.), 5$^{th}$ edition (2007).

Classification:
- *Family.*—Euphorbiaceae.
- *Species.*—*Euphorbia pulcherrima.*
- *Common name.*—Poinsettia.
- *Variety.*—'NPCW25442'.

Parentage:
- *Female.*—Poinsettia variety 'EP-2016-6142' (unpatented).
- *Male.*—Poinsettia variety 'NPCW19282' (U.S. Plant Pat. No. 32,726).

Plant:
- *Form.*—Triangular.
- *Growth habit.*—Wide, moderately upright.
- *Height.*—24 cm to 25 cm.
- *Width.*—43 cm to 45 cm.
- *Average number of inflorescences per plant.*—6 to 7.
- *Time to produce a cutting.*—5 weeks.
- *Flowering response time.*—Approximately 54 days.
- *Propagation type.*—Apical cuttings.
- *Rooting habit and root color.*—Freely branching and white (RHS NN155C).

Lateral branches:
- *Color.*—RHS 137B.
- *Length.*—15 cm to 17 cm.
- *Internode length.*—0.5 cm to 2.0 cm.
- *Diameter.*—0.4 cm to 0.7 cm.
- *Branching habit.*—Freely branching.
- *Number of lateral branches per plant.*—7 to 8.
- *Texture.*—Smooth.
- *Strength.*—Sturdy.

Leaves:
- *Quantity.*—5 to 6 per lateral branch.
- *Arrangement.*—Alternate.
- *Number of lobes on the leaf blade.*—None.

*Shape*.—Obtuse.
*Apex*.—Acuminate.
*Base*.—Rounded.
*Margin*.—Entire.
*Length*.—8 cm to 11 cm.
*Width*.—6 cm to 8 cm.
*Texture* (*both upper and lower surfaces*).—Upper: Smooth. Lower: Slightly pubescent.
*Vein color*.—Upper surface: Transparent. Lower surface: RHS 139D, slightly reddish towards the lower part of the middle vein.
*Variegation*.—Absent.
*Venation pattern*.—Reticulate.
*Color*.—Mature foliage: Upper surface: RHS 131A. Lower surface: RHS 139A. Immature foliage: Upper surface: RHS 141A. Lower surface: RHS 139D.
*Leaf petiole*.—Length: 3 cm to 4.5 cm. Diameter: 0.2 cm to 0.3 cm. Color: Upper (part) surface: RHS 59A. Lower (part) surface: RHS 181A. Texture: Smooth. Strength: Sturdy.
*Transitional leaves*.—Not visible.

Inflorescence:
*Type and habit*.—Cluster of cyathia.
*Quantity per lateral branch*.—1.
*Position relative to foliar plane*.—Above.
*Lastingness of inflorescence on the plant*.—4 weeks.
*Natural flowering season*.—November to December.
*Diameter*.—16 cm to 19 cm.
*Height*.—2 cm to 3 cm.
*Fragrance*.—Absent.

Bracts:
*Number of bracts per inflorescence*.—7.
*Shape*.—Obtuse.
*Apex*.—Acuminate.
*Base*.—Rounded.
*Margin*.—Entire.
*Size*.—Length: 5 cm to 10 cm. Width: 3 cm to 7 cm.
*Texture* (*both upper and lower surfaces*).—Smooth.
*Folding along the main vein*.—Absent.
*Twisting*.—Absent.
*Rugosity between the veins*.—Weak.
*Venation pattern*.—Reticulate.
*Vein color*.—Upper surface: RHS 183A. Lower surface: Close to RHS 182C.
*Bract color*.—Upper surface: Between RHS 46A and RHS 47A. Lower surface: Between RHS 46A and RHS 47A.
*Bract petiole*.—Length: 0.5 cm to 2 cm. Diameter: 0.2 cm. Color: Upper (part) surface: RHS 183A. Lower (part) surface: Close to RHS 182C. Texture: Smooth. Strength: Sturdy.

Cyme:
*Diameter*.—1.0 cm to 2.0 cm.
*Cyathia number*.—Approximately 4 per inflorescence.
*Deformation of glands of the cyathium*.—Absent.
*Timing of opening of cyathia*.—Beginning of December, first pollen appears in parallel to opening of the nectar cups, stigmas appear 2 weeks later.
*Cyathium*.—Shape: Ovate. Texture (inner and outer surfaces): Smooth. Diameter: 0.2 cm to 0.4 cm. Length: 0.3 cm to 0.5 cm. Color: RHS 143A.
*Peduncle*.—Color: RHS 142B. Length: 0.2 cm. Diameter: 0.1 cm. Texture: Smooth. Strength: Sturdy.
*Nectar cups*.—Number: 1 per cyathium. Diameter: 0.1 cm. Length: 0.3 cm to 0.6 cm. Color: Outward lips: RHS 12A. Inward lips: RHS 33A. Shape: Lip shaped. Texture (both inner and outer surfaces): Smooth.

Reproductive organs:
*Stamen quantity*.—10 to 20 per cyathium.
*Stamen shape*.—Ovate.
*Filament length*.—0.3 cm.
*Filament color*.—RHS 46A.
*Pollen quantity*.—Sparse.
*Pollen color*.—RHS 11A.
*Gynoecium*.—Absent.

Fruit and seed set: None observed.

Disease and insect resistance: No particular disease or insect resistance observed.

COMPARISON WITH PARENTAL LINES AND KNOWN VARIETY

'NPCW25442' is distinguished from its parents as described in Table 1:

TABLE 1

Comparison with Parental Lines

| Trait or characteristic | 'NPCW25442' | Female parent 'EP-2016-6142' | Male Parent 'NPCW19282' (U.S. Plant Pat. No. 32,726) |
|---|---|---|---|
| Bract color | Dark red | Greyish red | Rich red |
| Plant Habit | Wider than 'EP-2016-6142' and 'NPCW19282' | More upright than 'NPCW25442' | More upright than 'NPCW25442' |

COMPARISON WITH SIMILAR VARIETY

'NPCW25442' is most similar to the commercial poinsettia plant named 'NPCW22382' (unpatented). Differences between the two varieties are described in Table 2:

TABLE 2

| Trait or characteristic | 'NPCW25442' | Commercial variety 'NPCW22382' |
|---|---|---|
| Bract color | Darker red than 'NPCW22382' | Brighter red than 'NPCW25442' |
| Bract size | Smaller than 'NPCW22382' | Larger than 'NPCW25442' |

I claim:

1. A new and distinct variety of poinsettia plant named 'NPCW25442' as shown and described herein.

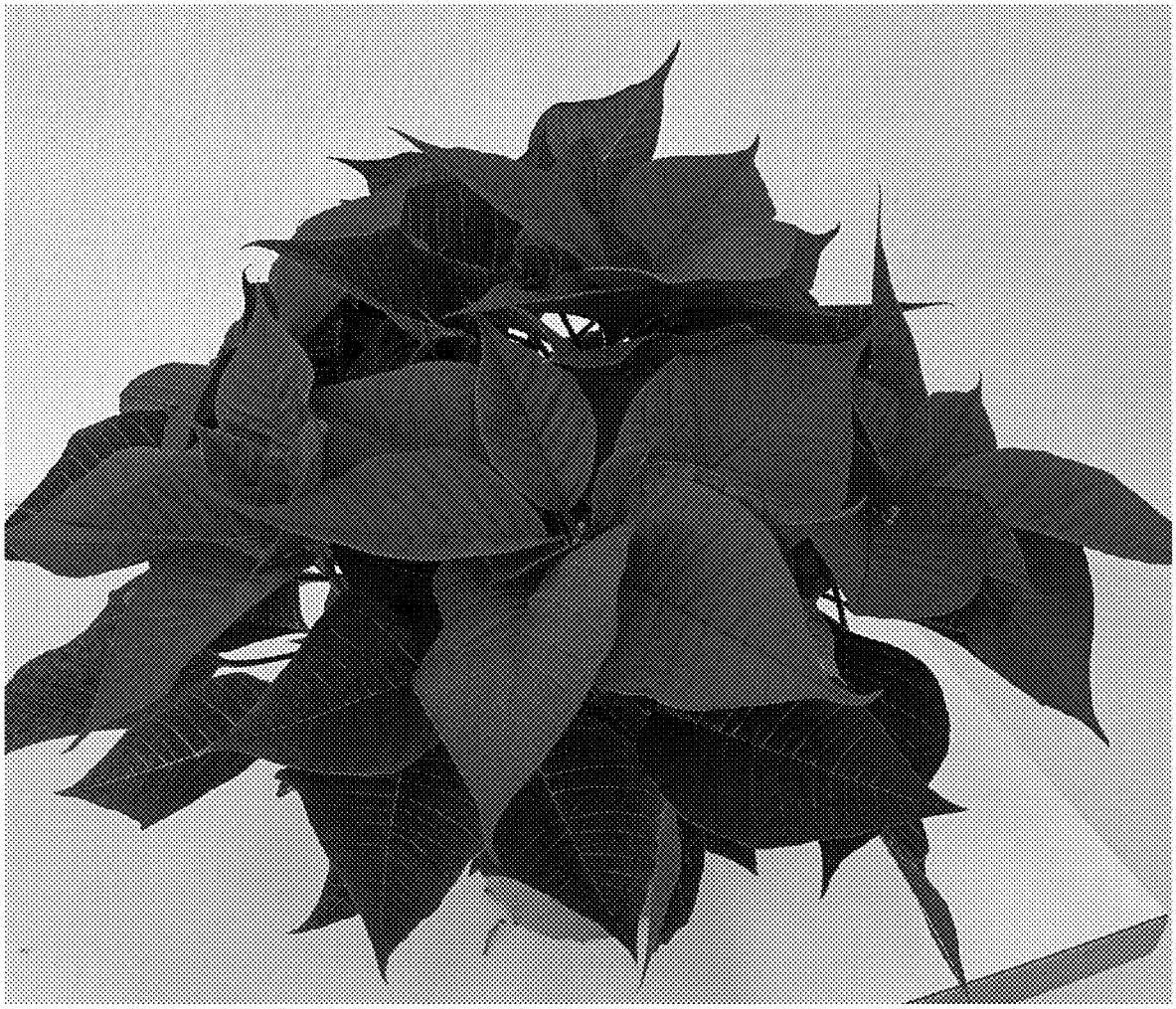

* * * * *